US00RE37449B1

(19) United States
(12) Reissued Patent
Kutney et al.

(10) Patent Number: US RE37,449 E
(45) Date of Reissued Patent: Nov. 13, 2001

(54) PROCESS OF SYNTHESIS OF 3',4'-ANHYDROVINBLASTINE, VINBLASTINE AND VINCRISTINE

(75) Inventors: James P. Kutney, Vancouver; Lewis S. L. Choi, Bunaby, both of (CA); Jun Nakano, Moriyama; Hiroki Tsukamoto, Kariya, both of (JP); Camille A. Boulet, Medicine Hat (CA); Michael McHugh, Glasgow (GB)

(73) Assignee: University of British Columbia, Vancouver (CA)

(21) Appl. No.: 09/437,626

(22) Filed: Nov. 10, 1999

Related U.S. Patent Documents

Reissue of:
(64) Patent No.: 5,047,528
Issued: Sep. 10, 1991
Appl. No.: 07/228,821
Filed: Aug. 2, 1988

U.S. Applications:
(

(63) Continuation-in-part of application No. 07/011,810, filed on Feb. 6, 1987, now abandoned.

(51) Int. Cl.[7] ..... C07D 519/04
(52) U.S. Cl. ..... 540/478; 540/479; 546/51
(58) Field of Search ..... 540/478

(56) References Cited

U.S. PATENT DOCUMENTS

| | | | |
|---|---|---|---|
| 4,144,237 | 3/1979 | Kutney | 540/478 |
| 4,199,505 | 4/1980 | Szantay et al. | 540/478 |
| 4,279,817 | 7/1981 | Kutney | 540/478 |
| 4,305,875 | 12/1981 | Potier et al. | 540/478 |
| 4,737,586 | 4/1988 | Potier et al. | 540/478 |
| 4,778,885 | 10/1988 | Vukovic et al. | 540/478 |
| 4,841,045 | 6/1989 | Kuehne | 540/478 |

FOREIGN PATENT DOCUMENTS

| | | |
|---|---|---|
| 2558124 | 7/1976 | (DE) . |
| 3801450 | 8/1988 | (DE) . |
| 3826412 | 2/1989 | (DE) . |

OTHER PUBLICATIONS

Kutney et al., Helvetica Chimica Acta, 59(8), pp. 2858–2882, 1976.
Fieser et al., "Reagents for Organic Synthesis", 6 pp. 36–37, Wiley–Interscience, John Wiley & Sons, New York, 1987.
Nishiyama et al., Chem. Abstr., 84: 179294h, 1976.
Nakumura et al., Chem. Abstr., 101: 229474j, 1984.
Langlois et al., Tetrahedron Letters, 14, pp. 1099–1102, 1976.
Mangeny et al., J. Am. Chem. Soc., 101(8), pp. 2243–2245, 1979.
Kutney et al., Heterocycles, 27(8), pp. 1845–1853, Aug. 1988.

*Primary Examiner*—Brenda Coleman
(74) *Attorney, Agent, or Firm*—Jenkens & Gilchrist

(57) ABSTRACT

The present invention relates to the synthesis of dimer alkaloid compounds, particularly those of the Catharantus (Vinca) family, from an indole unit, such as cantharanthine, and a dihydroindole unit, such as vindoline. A multi-step process is disclosed including the steps of (1) of 1,4-reduction of a first dimeric iminium intermediate to an enamine compound by reaction with a 1,4-dihydropyridine compound; (2) oxidative transformation of the resulting enamine to a second iminium intermediate under controlled aeration; (3) reduction of the second iminium intermediate to form the target dimer alkaloid compounds. The entire process can be conducted in a one-pot operation to obtain the target compounds without isolation of the intermediates.

40 Claims, No Drawings

PROCESS OF SYNTHESIS OF 3',4'-ANHYDROVINBLASTINE, VINBLASTINE AND VINCRISTINE

Matter enclosed in heavy brackets [ ] appears in the original patent but forms no part of this reissue specification; matter printed in italics indicates the additions made by reissue.

CROSS-REFERENCE TO RELATED U.S. APPLICATION

This application is a *reissue of Ser. No. 07/228,821 filed Aug. 2, 1988, now U.S. Pat. No. 5,047,528 which is a* continuation in part of pending U.S. application Ser. No. 07/011,810 filed Feb. 6, 1987, now abandoned.

BACKGROUND OF THE INVENTION

The present invention relates to the synthesis of dimer alkaloid compounds, particularly those of the Catharantus (Vinca) family, such as vinblastine, vincristine and leurosidine, sometimes referred to hereinafter as the target compounds or the target dimer alkaloid compounds.

The dimeric alkaloids of present interest have remarkable anti-viral, anti-tumor and anti-leukemic properties. In the past, these alkaloids were isolated from the Catharantus species, particularly C. roseus, in small quantities. More recently, progress has been made in the synthesis of these compounds (U.S. Pat. Nos. 4,144,237 and 4,279,817 to James P. Kutney, and parent application U.S. Ser. No. 07/011,810). Unfortunately, these prior art methods also yielded small quantities of the target compounds. The present invention overcomes the difficulties encountered in the prior art insofar as it yields dramatically increased quantities of the target dimer alkaloid compounds.

SUMMARY OF THE INVENTION

The present invention relates to the multi-step process for preparing dimer alkaloid compounds, particularly those of the Catharantus (Vinca) family, such as vinblastine, vincristine and leurosidine, as described in parent application U.S. Ser. No. 07/011,810, filed Feb. 6, 1987, the disclosure of which is incorporated herein by reference.

Briefly, the present process comprises the following steps:

(a) forming an N-oxide derivative in the cold at a temperature of from about −77° to about +40° C., from an indole unit having a bridge nitrogen, by oxidizing the bridge nitrogen and without isolating said derivative;

(b) treating said N-oxide derivative in the presence of at lest one member selected from the group consisting of acetic anhydride, halogenated acetic anhydride, and acetyl chloride, to effect a polonovski-type fragmentation reaction;

(c) without isolating the product of step (b), stereospecifically coupling said product of step (b) with a dihydroindole unit in the presence of at least one member selected from the group consisting of acetic anhydride, halogenated acetic anhydride, and acetyl chloride at a low temperature of about −70° C. to about +40° C., under inert conditions, to form a first iminium intermediate;

(d) reducing said first iminium intermediate by reaction with a 1,4-dihydropyridine compound, thereby forming an enamine;

(e) preparing a second iminium intermediate by oxidative transformation of the enamine obtained in step (d) under controlled aeration conditions; and (f) reducing the product obtained in step (e) to form the target dimer alkaloid compounds.

All of the above steps can be conducted in a one-pot operation from the reaction of the indole unit and the dihydroindole unit to the final products without isolation of the intermediates.

DETAILED DESCRIPTION OF THE INVENTION

The present invention relates to the synthesis of dimer alkaloid compounds, particularly of the Catharantus (Vinca) family, such as vincristine, vinblastine and leurosidine, as represented by the following formula I:

I

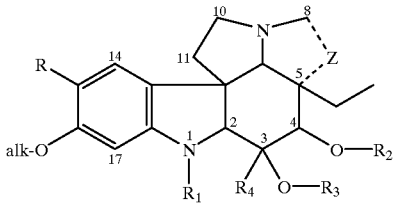

wherein in Formula I, alk=$CH_3$ or $(CH_2)_nCH_3$ where N=1–5;

$R_1$=$CH_3$ or CHO;

$R_2$=H or CO-alk;

$R_3$=H;

$R_4$=COO-alk or $CONR_{13}R_{14}$ wherein $R_{13}$ $R_{14}$ are selected from the group consisting of hydrogen, alkyl, substituted alkyl, aryl or substituted aryl Z=—CH=CH— or —$CH_2$—$CH_2$—;

R=II or IIa;

II

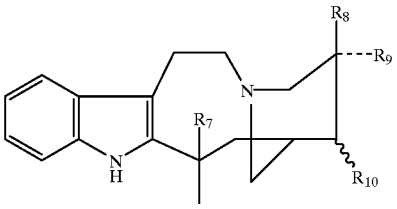

wherein, $R_7$=H or COO-alk;

$R_8$=H, OH, O-alk, OCO-alk or alkyl;

$R_9$=H, OH, O-alk, OCO-alk or alkyl;

$R_{10}$=H, OH, O-alk, OCO-alk;

$R_{11}$=H or COO-alk; and $R_{12}$=H or alkyl.

When, in Formula I, alk=$CH_3$, $R_1$=$CH_3$, $R_2$=CO—$CH_3$, $R_3$=H, $R_4$=$COOCH_3$, Z=—CH=CH—, R=Formula II, $R_7$=$COOCH_3$, $R_8$=OH, $R_9$=$C_2H_5$ and $R_{10}$=H, the product is vinblastine; when alk=$CH_3$, $R_1$=$CH_3R_2$=CO—$CH_3$, $R_3$=H, $R_4$=$COOCH_3$, Z=—CH=CH—, R=Formula II, $R_7$=$COOCH_3$, $R_8$=$C_2H_5$, $R_9$=OH and $R_{10}$=H, the product is leurosidine; and when alk=$CH_3R_1$=CHO, $R_2$=CH—$CH_3R_3$=H, $R_4$=$COOCH_3Z$=—CH=CH—, R=Formula II, $R_7$=$COOCH_3$, $R_8$=OH, $R_9$=$C_2H_5$ and $R_{10}$=H, the product is vincristine.

Throughout this disclosure, alk and alkyl represent a $C_1$–$C_6$ alkyl, and preferably $C_1$–$C_3$ alkyl, and aryl represents a mono-aryl such as benzyl, xylyl, etc. All percentages are percentages by weight, all time periods are in minutes, and all temperatures are in °C., unless otherwise specifically noted.

The present process of preparing the target dimeric alkaloids comprises the initial formation of an N-oxide derivative from an indole unit as represented by Formula III, IIa

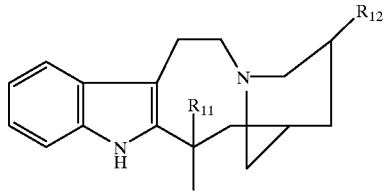

III

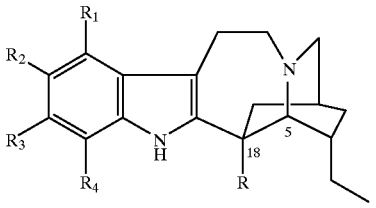

wherein R represents hydrogen or COO-alk and $R_1$, $R_2$, $R_3$ and $R_4$, independently, represents H, OH, O-alk, OCO-alk, alkyl or aryl. The indole unit is oxidized by oxidizing the bridge nitrogen to form an N-oxide derivative as represented by Formula III(a)

IIIa

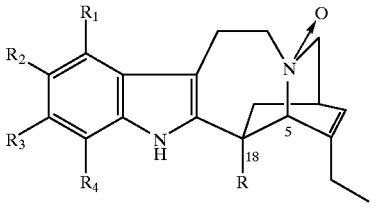

and related analogues as represented by Formula III(b)

IIIb

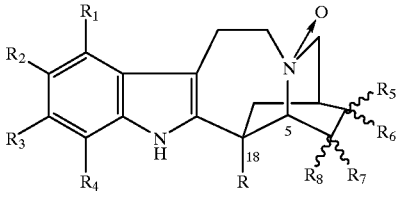

wherein $R_1$, $R_2$, $R_3$, and $R_4$ are the same as Formula III, and $R_5$, $R_6$, $R_7$ and $R_8$, independently, represent H or an alkyl group represented by the Formula $(CH_2)_n$ $CH_3$ where n=0–10. Preferably, the indole unit utilized in step (a) is catharanthine (Formula III when R=$COOCH_3$ and $R_1$, $R_2$, $R_3$, and $R_4$ are H).

The N-oxide derivative is oxidized at the bridge nitrogen at a temperature in the range of about −77° C. to about −40° C. by reaction with a peracid such as m-chloroperbenzoic acid or p-nitroperbenzoic acid in an inert organic solvent such as methylene chloride or other polyhalo organic solvents (step (a)). The N-oxide intermediate thus formed is used in the next step (step (b)) without isolation. The thus-treated N-oxide derivative obtained in step (a) undergoes a fragmentation reaction (step (b)) and the iminium intermediate thus formed is coupled (step (c)) with a dihydroindole unit, such as vindoline, as represented by Formula IV,

IV

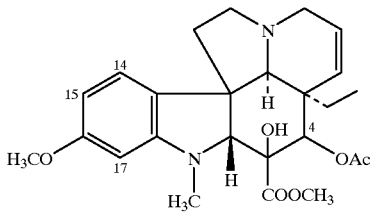

in which the two respective compounds (Formula IIIa and Formula IV) are linked via a carbon-carbon bond involving the aliphatic center $C_{18}$ in the N-oxide derivative and an aromatic carbon $C_{15}$ in the dihydroindole unit.

The fragmentation reaction which fragments the $C_5$–$C_{18}$ bond of the indole N-oxide derivative is carried out in the presence of a reagent such as trifluoroacetic anhydride. To maximize the subsequent coupling reaction which promotes the formation of a natural dimer bonded at $C_{18}$ (indole unit) and $C_{15}$ (dihydroindole unit), the dihydroindole unit may be added to the reaction. As alternative reagents for the trifluoroacetic anhydride component used in fragmentation and coupling, there may be utilized trichloroacetic anhydride. These reagents bring about a Polonovski-type fragmentation of the $C_5$–$C_{18}$ bond in the compounds shown in Formulae IIIa and IIIb.

The reaction temperature, time and pressure conditions in general are similar to those employed in the Polonovski reaction which, in its original application, involved the dealkylation of tertiary and heterocyclic amines by acylation of the corresponding N-oxides with acetic anhydride or acetyl chloride (cf. Merck Index, 8th ed., 1986, page 1203). The temperature of the fragmentation and coupling steps may vary from about −70° C. to about 40° C.; preferably from about −70° C. to about −30° C., and most preferably from about −60° to about −40° C. The formation of the N-oxide derivative, the fragmentation step and the coupling step, may be conducted in the open or under cover in an inert gas atmosphere such as argon or any other inert gas of Group Zero of the Periodic Table such as helium, neon, etc. or nitrogen. Due to the low temperature necessary for the later stage reactions, the reaction time for each of steps (a)–(c) may vary from several minutes to several days. Typically, step (a) would take from about 5 min. to about several hours, step (b) would take from about 5 min. to about 1 hour, and step (c) would take from about 10 min. to about several hours.

The above-described conditions for the coupling reaction in the present process represent an important improvement over the prior art (as described, for example, in U.S. Pat. No. 4,279,817; Helv. Chim. Acta, 59, 2858 (1976) and in Reaction Scheme I). In particular, the present coupling (step (c)) allows for the preparation and isolation of a relatively unstable dihydropyridinium intermediate, formed in the coupling of the N-oxide derivative and the dihydroindole unit.

REACTION SCHEME I
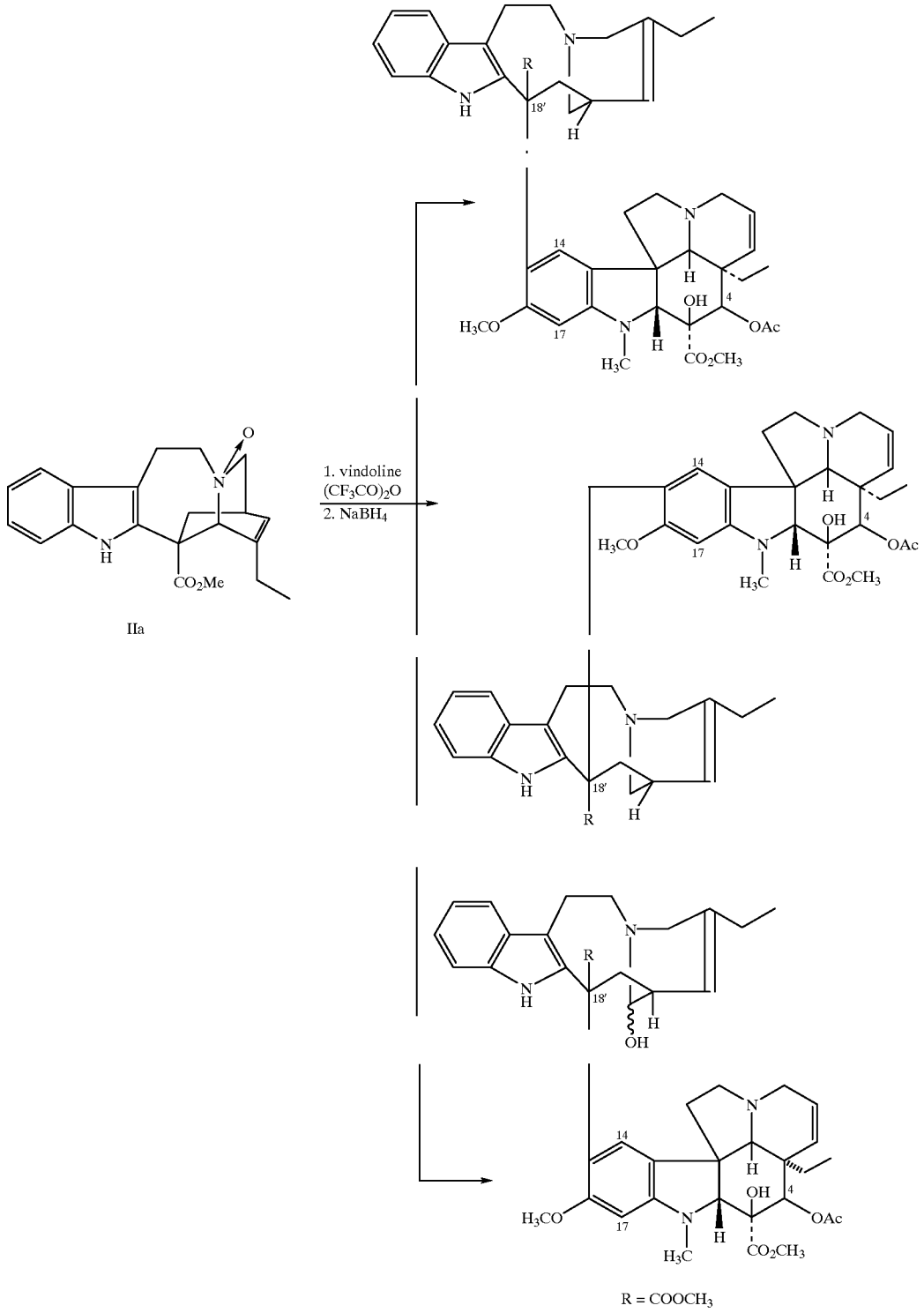

The relatively unstable indole-dihydroindole dimer intermediate formed by the stereospecifically coupling step (c) is characterized by an iminium salt function at the $N_b$ atom of the indole moiety. The unstable dimer is hereinafter referred to as an iminium intermediate. The iminium intermediate is represented by Formulas V or VI

V

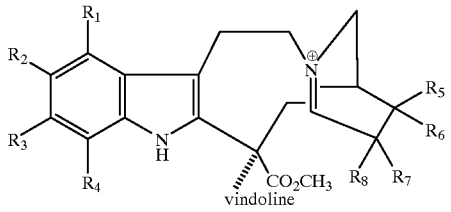

wherein $R_1$, $R_2$, $R_3$, $R_4$, $R_5$, $R_6$, $R_7$, and $R_8$ are as previously discussed.

The prior art method, as described in U.S. Pat. No. 4,279,817, reduces this unstable iminium intermediate by reaction with alkali metal borohydride ($NaBH_4$, $KBH_4$, $LiBH_4$) to obtain certain stable dimeric alkaloids. For instance, reduction of the iminium intermediate of Formula VI by reaction with alkali metal borohydride, gives the 3',4'-dehydrovinyblastine compound as represented by Formula VII and shown in reaction scheme II.

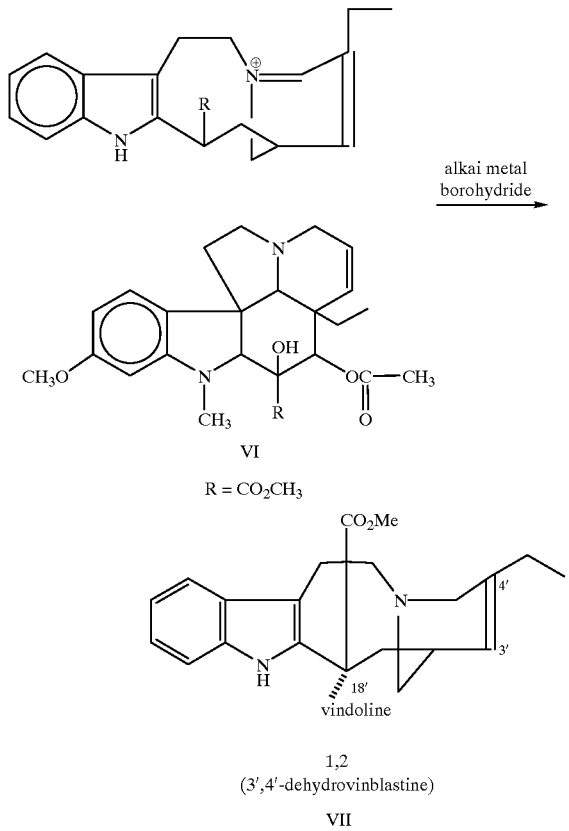

In the present invention, however, the relatively unstable iminium intermediate (Formula V or VI) need not be reduced and, in fact, may be isolated by various chromatographic techniques. For example, said iminium intermediate may be isolated by applying the reaction mixture of step (c) directly onto an appropriate chromatographic system such as column, thin layer or high performance liquid chromatography, preferably reverse phase and/or size-exclusion separation methods. The temperature of the operation may vary from about 40° C. to about room temperature. Alternatively, volatile reagents and solvents which are present together with the iminium intermediate in the reaction mixture may be removed under reduced pressure and temperature, preferably below −10° C., and below about 5 mm. Hg. The resulting solid (Formula V or VI) is then dissolved in a suitable organic solvent, such as halogenated hydrocarbons, ethers, alcohols, acetonitrile, or the like or in various aqueous buffer solutions. The pH of the buffer solution may vary from about 2 to about 10. Suitable aqueous buffer solutions include, for example, phosphate, Tris HCl, and MES buffers. The solution of iminium intermediate (Formula V or VI) can then be purified by the chromatographic methods described above. Alternatively, the iminium intermediate solution can be used directly for subsequent reactions.

Example 1 shows the preparation of the iminium intermediate by reaction of the catharanthine, (the indole unit of Formula III when R=$COOCH_3$ and $R_1$, $R_2$, $R_3$ and $R_4$=H) with vindoline (the dihydroindole unit of Formula IV).

EXAMPLE 1

Preparation of the Iminium Intermediate (Formula VI) via Modified Polonovski Reaction The reaction was performed under anhydrous conditions. All glassware was oven-dried at 120° C. The solvent, methylene chloride, and coupling reagent, trifluoroacetic anhydride, were distilled from $P_2O_5$ prior to use.

To a solution of catharanthine (Formula III, 200 mg, 0.6 mmol) in dry methylene chloride (2 ml) at −20° C. under a positive atmosphere of argon was added m-chloroperbenzoic acid (132 mg, 0.8 mmol), and the mixture was stirred for 5 minutes. To the catharanthine N-oxide (IIIa; R=$COOCH_3$; $R_1$, $R_2$, $R_3$, and $R_4$=H), thus formed was added a solution of vindoline (IV, 270 mg, 0.6 mmol) in methylene chloride (1 ml) and the mixture was cooled to −60° C. Trifluoroacetic anhydride (0.2 ml, 1.5 mmol) was added to the stirred reaction mixture maintained at −60° C. for 2 hours. After this time, the solvent and excess reagents were removed in vacuo at −20° C. to leave a reddish-brown residue containing the iminium intermediate. The intermediate was characterized by reverse phase high performance liquid chromatography (HPLC) (Waters Radial-Pak $C_{18}$ or CN cartridge, methanol-$H_2O$-$Et_3N$ as solvent system). It was shown that the yield of the iminium intermediate of Formula VI in this reaction exceeded 80%.

The iminium intermediate (Formulae V or VI) was then converted to an enamine compound by reducing the iminium intermediate with a 1,4-dihydropyridine as illustrated, for example, in reaction scheme III:

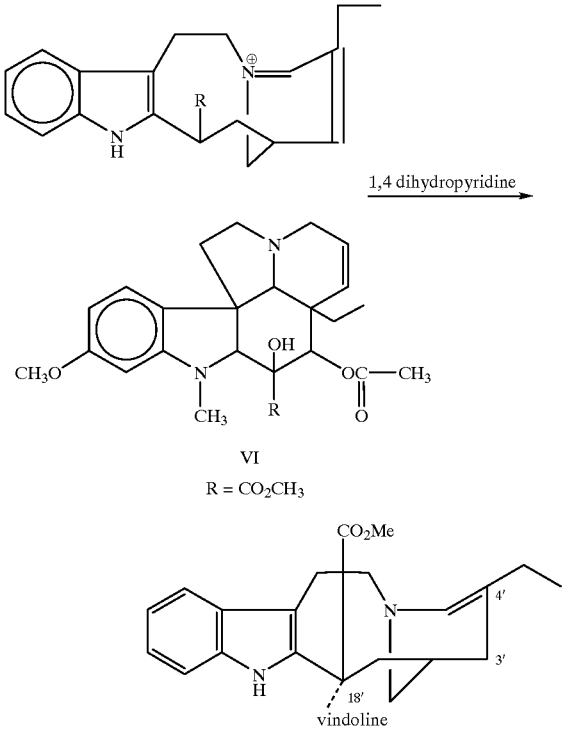

As indicated above, the conversion may take place either after isolating the iminium intermediate or by treating the reaction mass obtained in step (c). Production of the target compound is dependent upon which iminium intermediate is employed. In other words, the iminium intermediate V leads to analogs of vinblastine, and iminium intermediate VI leads to the target compounds vinblastine and leurosidine. Vincristine, in turn, is produced by the oxidation of vinblastine, specifically, the oxidation of the $R_1$ substituent methyl group. For example, one method for the oxidation of said methyl group by reacting the vinblastine with Jones reagent ($CrO_3$) in acetone and acetic anhydride at very low temperature, such as −78° C. (J. P. Kutney et al, Heterocycles, Vol. 9, p. 201, 1978). In order to limit to confusion, however, the following discussion will be directed to the iminium intermediate of Formula VI. Note however, analogous steps can be conducted with the iminium intermediate of Formula V.

When the starting indole unit has a $C_3$–$C_4$ double bond (e.g. catharanthine (Formula III when R═$COOCH_3$ and $R_1$, $R_2$, $R_3$, and $R_4$=H), the resultant coupling intermediate contains an alpha, beta-unsaturated iminium functional group as represented by Formula VI. This iminium intermediate can be converted in step (d), via a 1,4-reduction to the enamine represented by Formula VIII:

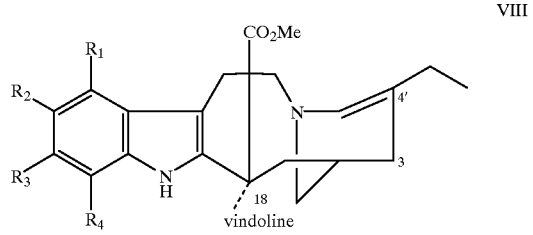

Reagents used for this reduction include 1,4-dihydropyridine compounds (the so-called NADH models) as represented by Formula IX:

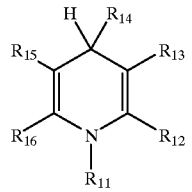

wherein $R_{11}$, $R_{12}$, $R_{13}$, $R_{14}$, $R_{15}$ and $R_{16}$, independently, can be H, alkyl, substituted alkyl, aryl and substituted aryl. The term "substituted" is meant to include, for example, the following substituents: alkyl, carboxy, alkoxy, aryl, aryloxy, amino, carboxyamino, sugar units, carboxyalkyl and salts thereof. The term aryl includes N-containing heterocyclic ring structures, for example, pyrrolidine, which may further be substituted by $CONR_{19}R_{20}$, wherein $R_{19}$ and $R_{20}$ are H or alkyl. Two series of such compounds are readily available [Chem. Rev. 82, 232 (1982); Chem. Rev. 72, 1 (1972)]. The first series is known as Hantzch esters wherein $R_{13}$ and $R_{15}$ in Formula IX are carboxylic esters, e.g. $COOC_2H_5$. The second series if the N-substituted 1,4-dihydronicotinamides (Formula IX) in which $R_{11}$ is a substituted alkyl or substituted aryl function, e.g. benzyl, and $R_{13}$ is $CONR_7R_8$ wherein $R_{17}$ and $R_{18}$, independently, can be hydrogen, alkyl, substituted alkyl, aryl and substituted aryl.

One preferred class of 1,4-dihydropyridines which may be employed in the 1,4-reduction are selected from 1,4-dihydropyridine compounds of Formula IX wherein $R_{12}$, $R_{14}$, $R_{15}$ and $R_{16}$ are hydrogen, $R_{11}$ is alk-aryl and $R_{13}$ is —CN or

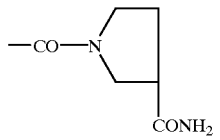

Another preferred class of 1,4-dihydropyridines are the 1,4-dihydronicotinamides wherein $R_{12}$, $R_{14}$, $R_{15}$ and $R_{16}$ are hydrogen, $R_{13}$ is $CONH_2$ and $R_{11}$ is a functional group such as alk-aryl, carboxylic esters, sugars, carboxylic acids and carboxylate salts.

Most preferably, 1,4-dihydronicotinamides are employed in the reduction, wherein $R_{11}$ is selected from the electron rich functional group consisting of carboxylic esters and carboxylate salts. Extensive research has shown that these 1,4-dihydronicotinamides, provided with such electron rich functional groups, are particularly capable of coordination with the positively charged iminium intermediate (e.g. Formula VI), increasing both regioselectivity (i.e. 1,4-reduction over 1,2-reduction) and the rate of the reduction of the iminium intermediate (Formula VI), thus leading to an improved yield of the enamine (Formula VIII). Specific examples of these preferred and most preferred 1,4-dihydropyridine compounds are provided in Table 1 (Formulae IX-A to IX-J).

TABLE I

| Formula | Reducing Agents | Procedure | Reducing Agents | Procedure | Formula |
|---|---|---|---|---|---|
| | 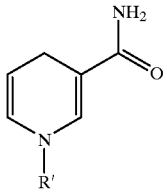 | | 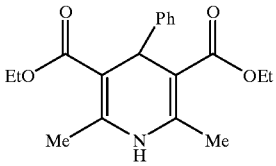 | B | IX-B |
| IX-A<br>IX-C | R' = $CH_2C_6H_5$<br>= $CH(C_6H_5)_2$ | A<br>C | 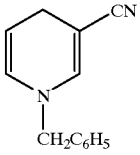 | D | IX-D |
| IX-F = | 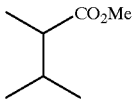 | F | 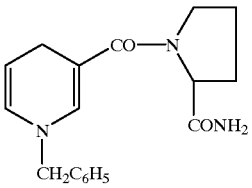 | E | IX-E |
| IX-G = | 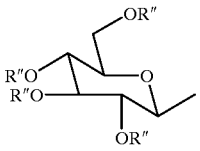 <br>R" = Ac | G | | | |
| IX-H = | 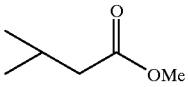 | H | | | |
| IX-I = | 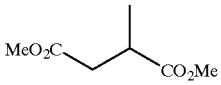 | I | | | |
| IX-J = | 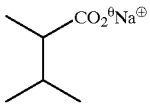 | J, K | | | |

The above reductants can be used alone or in combination. The reduction is conducted under an inert atmosphere such as argon or an inert gas of Group Zero of the Period Table (helium, neon, etc.) or nitrogen. Various solvents may be employed during the reduction step (d). Suitable solvents include, for example, alcohols, acetonitrile or higher members of this series, dimethyl sulfoxide, dimethylformamide, various ethers such as dioxane and tetrahydrofuran and chlorinated hydrocarbons, normally without an aqueous buffer.

The progress of the reduction step (d) is monitored by direct analysis of the reaction mixture on an appropriate chromatographic system, preferably reverse phase high performance liquid chromatography. This method is used to optimize the reaction temperature, time, pressure and concentration of reactants. The reaction temperature may vary from about −60° to about +60° C., and preferably from about −60° to about +20° C. The reaction time may vary from several minutes to several days depending on other parameters.

The following experimental examples (Examples 2–12, procedures A to K) were conducted for the synthesis of the enamine from the iminium intermediate by reaction with the reducing agents of Table I, in accordance with reaction scheme III.

EXAMPLE 2

Reduction of Iminium Intermediate (Formula VI) with 1-Benzyl-1,4-dihydronicotinamide [Formula IX, $R_1$=benzyl, $R_2$, $R_4$, $R_5$, and $R_6$=H; $R_3$=$CONH_2$; (Formula IX-A) Procedure A]

To a stirred solution of iminium intermediate (VI, 100 mg) in degassed acetonitrile (5 ml) was added 1-benzyl-1,4-dihydronicotamide (135 mg, 0.63 mmol, 6 equivalents) under a positive atmosphere of argon (greater than 760 mm Hg) at room temperature (20° C.) over a period of 5 hours. After this time, the reaction mixture, as monitored by reverse phase HPLC (Waters Radial-Pak $C_{18}$ or CN cartridge, methanol/$H_2O$/$Dt_3N$ solvent system), indicated complete conversion of VI to a mixture of enamine VIII and 3',4'-dehydrovinblastine (VII) in a ratio of 1:1 (75% yield).

EXAMPLE 3

Reduction of Iminium Intermediate (Formula VI) with 1-Benzyl-1,4-dihydronicotinamide (Formula IX, $R_1$=benzyl, $R_2$, $R_4$, $R_5$, and $R_6$=H; $R_3$=$CONH_2$ (Formula IX-A) Procedure A]

To a stirred solution of iminium intermediate (VI, 100 mg) in methanol (5 ml) kept initially at 0° C for 0.5 hours was added dropwise or in portions, a solution of 1-benzyl-1,4-dihydronicotinamide (56 mg, 0.26 mmol, 2.5 equivalents) in methanol (2ml) under a positive atmosphere of argon (greater than 760 mm Hg) over a period of 5 hours. During this time the solution was allowed to warn up to room temperature. HPLC monitoring, as in Example 1, indicated complete conversation of VI to a mixture of enamine VIII and 3',4'-dehydrovinblastine (VII) in a ratio of 1:1 (75% yield).

EXAMPLE 4

The mixture of enamine (VIII) and 3',4'-dehydrovinblastine (VII) obtained as described in Example 2 above, was treated with excess sodium borohydride (500 mg) at 0° C. The reaction mixture was then made basic with $NH_4OH$ and extracted with ethyl acetate (3×200 ml). The combined organic phase was dried over magnesium sulphate. The product obtained, after removal of organic solvent, was subjected to preparative thin layer chromatography or silica gel (methanol/ethyl acetate as eluting system). The product was shown to be a mixture of unreacted 3',4'-dehydrovinblastine (VII), and the known compounds 4'-deoxovinblastine (X, R=$COOCH_3$) and 4'-deoxo-4'-epivinblastine (XI, R=$COOCH_3$). The presence of the latter compounds provided unambiguous evidence for the structure of enamine VIII.

EXAMPLE 5

The procedure of Example 4 was repeated, except that the mixture obtained in Example 3 was treated with excess sodium borohydride instead of the mixture from Example 2. The product was again shown to be a mixture of unreacted 3',4'-dehydrovinblastine (VII), and the known compounds 4'-deoxovinblastine (X, R=$COOCH_3$) and 4'-deoxo-4'-epivinblastine (XI, R=$COOCH_3$). The presence of the latter compounds provided unambiguous evidence for the structure of enamine VIII.

EXAMPLE 6

Reduction of Iminium Intermediate (Formula VI) with 3,5-diethoxycarbonyl-2,6-Dimethyl-4-Phenyl-1,4 Dihydropyridine [Formula IX, $R_1$=H; $R_3$, and $R_5$, $COOCH_2CH_3$; $R_2$ and $R_6$=$CH_3$; $R_4$=phenyl; (Formula IX-B)—Procedure B]

To a stirred solution of iminium intermediate (VI, 100 mg) in degassed acetonitrile (3 ml) was added 3,5-diethoxycarbonyl-2,6-dimethyl-4-phenyl-1,4-dihydropyridine (264 mg, 8 equivalents) in ethanol (12 ml) under a positive atmosphere of argon (greater than 760 mm Hg) and at a temperature of about −20 to about 40° C. The reaction mixture was refluxed for 3 hours. After this time, reverse phase HPLC analysis (as described above) indicated, among other products, formation of enamine VIII and 3',4'-dehydrovinblastine (VI) in a ratio of 1:1 (60% yield).

EXAMPLE 7

Reduction of Iminium Intermediate (Formula VI) with 1 Diphenylmethyl-1,4-dihydronicotinamide [Formula IX, $R_1$=diphenyl methyl; $R_2$, $R_4$, $R_5$, and $R_6$=H; $R_3$=$CONH_2$; (Formula IX-C)—Procedure C]

To a stirred solution of iminium intermediate (VI, 100 mg) in degassed ethanol (6 ml) was added 1-diphenylmethyl-1,4-dihydronicotinamide (Formula IX-C) (76 mg, 2.5 equivalents) in methanol (6 ml) under a positive atmosphere of argon (greater than 760 mm Hg) and at a temperature of 20° C., the reducing agent being added portionwise at the rate of 1 equivalent each 60 min. After this, reverse phase HPLC analysis (Waters Radial-Pak $C_{18}$ or CN cartridge, methanol-$H_2O$-$Et_3N$ as solvent system) indicated, among other products, formation of enamine (VIII) and 3',4'-dehydrovinblastine (VII) in a ratio of 0.9:1 (60% yield).

EXAMPLE 8

Reduction of Iminium Intermediate (Formula VI) with 1-Benzyl-3-cyano-1,4-dihydropyridine [Formula IX, $R_1$=benzyl; $R_2$, $R_4$, $R_5$, and $R_6$=H; $R_3$=CN; (Formula IX-D)—Procedure D]

To a stirred solution of iminium intermediate (VI, 100 mg) in degassed methanol (6 ml) was added 1-benzyl-3-cyano-1,4-dihydropyridine (Formula IX-D) (206 mg, 10 equivalents) in methanol (10 ml) under a positive atmosphere of (greater than 760 mm Hg) argon and at a temperature of 20° C., the reducing-agent being added portionwise at the rate of 1 equivalent each 60 min. After this, reverse phase HPLC analysis (as described above) indicated, among other products, formation of enamine (VIII) and 3',4'-dehydrovinblastine (VII) in a ratio of 1:1 (40% yield).

EXAMPLE 9

Reduction of Iminium Intermediate (Formula VI) with 1-benzyl-1,4-dihydronicotinyl-(2'-carbamoyl pyrrolidinyl)-amide [Formula IX, $R_1$=benzyl; $R_2$, $R_4$, $R_5$, and $R_6$=H; $R_3$=(2'carbamoylpyrrolidinyl) carbonyl; (Formula IX-E)—Procedure E]

To a stirred solution of iminium intermediate (VI, 100 mg) in degassed methanol (6 ml) was added 1-benzyl-1,4-dihydronicotinyl-(2'carbamoylpyrrolidinyl)-amide (Formula IX-E) (163 mg, 5 equivalents) in methanol (5 ml) under a positive pressure of argon (greater than 760 mm Hg)

and at a temperature of 20° C., the reducing agent being added portionwise at the rate of 1 equivalent each 30 min. After this, reverse-phase HPLC analysis (as described above) indicated, among other products, formation of enamine (VIII) and 3',4'-dehydrovinblastine (VII) in a ratio of 1.1:1 (60% yield).

EXAMPLE 10

Reduction of Iminium Intermediate (Formula VI) with 1,4-dihydro-1-(1methoxycarbonyl isobutyl) nicotinamide [Formula IX, $R_1$-1-methoxycarbonyl isobutyl; $R_2$, $R_4$, $R_5$, and $R_6$=H; $R_3$=$CONH_2$; (Formula IX-F)—Procedure F]

To a stirred solution of iminium intermediate (VI, 100 mg) in degassed methanol (6 ml) was added 1,4-dihydro-1-(1-methoxy carbonylisobutyl)-nicotinamide (Formula IX-F) (150 mg, 6 equivalents) in methanol (6 ml) under a positive pressure of argon (greater than 760 mm Hg) and at a temperature of 20° C., the reducing agent being added portionwise at the rate of 1 equivalent each 30 min. After this, reverse-phase HPLC analysis (as described above) indicated, among other products, formation of enamine (VIII) and 3',4'-dehydrovin-blastine (VII) in a ratio of 2:2 (65% yield).

EXAMPLE 11

Reduction of Iminium Intermediate (Formula VI) with 1 (2',3',4', 6'-Tetraacetyl-(beta)-D-glucopyranosidyl)-1,4-dihydronicotinamide [Formula IX, $R_1$=(2',3',4',6'-Tetraacetyl-(beta)-D-glucopyranosidyl; $R_2$, $R_4$, $R_5$, and $R_6$=H; $R_3$=$CONH_2$; (Formula IX-G)—Procedure G]

To a stirred solution of iminium intermediate (VI, 100 mg) in degassed methanol (6 ml) was added 1-(2',3',4',6'-Tetra-acetyl-(beta)-D-glycopyranosidyl)-1,4-dihydronicotinamide (Formula XXIX) (238 mg, 5 equivalent in methanol (10 ml) under a positive atmosphere of argon (greater than 750 mm Hg) and at a temperature of 20° C., the reducing agent being added portionwise at the rate of 1 equivalent each 60 min. After this, reverse-phase HPLC analysis (as described above) indicated, among other products, formation of enamine (VIII) and 3',4'-dehydrovinblastine (VII) in a ratio of 1.5:1 (70l % yield).

EXAMPLE 12

Reduction of Iminium Intermediate (Formula VI) with 1,4-Dihydro-1-(2'methoxycarbonyl isopropyl) nicotinamide [Formula IX, $R_1$=2'-methoxy carbonylisopropyl; $R_2$, $R_4$, $R_5$, and $R_6$=H; $R_3$=$CONH_2$; (Formula IX-H)—Procedure H]

To a stirred solution of iminium intermediate (VI, 100 mg) in degassed methanol (6 ml) was added 1,4-dihydro-1-(2'-methoxy-carbonylisopropyl-nicotinamide (Formula IX-H) (82 mg, 3.5 equivalents) in methanol (7 ml) under a positive atmosphere of argon (greater than 760 mm Hg) and at a temperature of 20° C., the reducing agent being added portionwise at the ate of one equivalent each 30 min. After this, reverse-phase HPLC analysis (as described above) indicated, among other products, formation of enamine (VIII) and 3', 4'-dehydrovinblastine (VII) in a ratio of 1.1:1 (65% yield).

EXAMPLE 13

Reduction of Iminium Intermediate (Formula VI) with 1,4-Dihydro-(1',2'-dimethoxy carbonyl ethyl)-nicotinamide [Formula IX, $R_1$=1',2'-dimethoxy carbonyl ethyl; $R_2$, $R_4$, $R_5$, and $R_6$=H; $R_3$=$CONH_2$; (Formula IX-I)—Procedure I]

To a solution of iminium intermediate (VI, 100 mg) in degassed methanol (6 ml) was added 1,4-dihydro-1-(1',2'-dimethoxy carbonyl ethyl)-nicotinamide (Formula IX-I) (148 mg, 5 equivalents) in methanol (10 ml) under a positive atmosphere of argon, (greater than 760 mm Hg) and at a temperature of 20° C., the reducing agent being added portionwise at the rate of 1 equivalent each 30 min. After this, reverse-phase HPLC analysis (as described above) indicated, among other products, formation of enamine (VIII) and 3',4'-dehydrovinblastine (VII) in a ratio of 1.1:1 (70% yield).

EXAMPLE 14

Reduction of Iminium Intermediate (Formula VI) with 1,4-Dihydro-1-(sodium-isobutyl-1-carboxylate) nicotinamide [Formula IX, $R_1$=sodium-isobutyl-1-carboxylate; $R_2$, $R_4$, $R_5$, and $R_3$=$CONH_2$; (Formula IX-J)—Procedure J]

To a solution of iminium intermediate (VI, 100 mg) in degassed methanol (6 ml) was added 1,4-dihydro-1-(sodium-isobutyl-1-carboxylate)-nicotinamide (Formula IX-J) (130 mg, 5 equivalents) in methanol (6 ml) under a positive atmosphere of argon (greater than 760 mm Hg) and at a temperature of 20° C., the reducing agent being added portionwise at the rate of 1 equivalent each 30 min. After this, reverse-phase HPLC analysis (as described above) indicated, among other products, formation of enamine (VIII) and 3',4'-dehydrovinblastine (VII) in a ratio of 2.2:1 (70% yield).

EXAMPLE 15

Reduction of Iminium Intermediate (Formula VI) with 1,4-Dihydro-1-(sodium-isobutyl-1-carboxylate) nicotinamide [Formula IX, $R_1$=sodium-isobutyl-1-carboxylate; $R_2$, $R_4$, $R_5$, and $R_6$=H; $R_3$=$CONH_2$; (Formula IX-J) at low temperature—Procedure K]

To a solution of iminium intermediate (VI, 100 mg) in degassed methanol (6 ml) at −20° C. was added 1,4-dihydro-1-(sodium-isobutyl-1-carboxylate)-nicotinamide (Formula IX-J) (155 mg, 6 equivalents) in methanol (6 ml) under a positive atmosphere of argon, (greater than 760 mm Hg) the reducing agent being added in one portion. After 45 min. at this temperature, reversephase HPLC analysis (as described above) indicated, among other products, formation of enamine (VIII) and 3',4'-dehydrovinblastine (VIIX) in a ratio of 3.2:1 (80% yield).

EXAMPLE 16

The procedure of Example 15 was repeated, except that the reaction was carried out at −40° C. After 60 minutes, enamine (VIII) and 3',4'-dehydrovinblastine (VII) were obtained in a ratio of 4.2:1 (85% yield). The process of this example is designated as Procedure L.

Results of Examples 2–16 are summarized in Tables 2 and 3.

TABLE 2

Effect of Reducing Agent on 1,4- vs. 1,2-Reduction of Iminium VI

| Example Numbers | Reduction Procedure | 1,4:1,2-Reduction Products[1] | Yield[2] (%) |
|---|---|---|---|
| 2, 3 | A | 1:1 | 75 |
| 6 | B | 1:1 | 60 |
| 7 | C | 0.9:1 | 60 |

TABLE 2-continued

Effect of Reducing Agent on 1,4- vs. 1,2-Reduction of Iminium VI

| Example Numbers | Reduction Procedure | 1,4:1,2-Reduction Products[1] | Yield[2] (%) |
|---|---|---|---|
| 8 | D | 1:1 | 40 |
| 9 | E | 1.1:1 | 60 |
| 10 | F | 2:1 | 65 |
| 11 | G | 1.5:1 | 70 |
| 12 | H | 1.1:1 | 65 |
| 13 | I | 2.3:1 | 70 |
| 14 | J | 2.2:1 | 70 |
| 15 | K | 3.2:1 | 80 |
| 16 | L | 4.2:1 | 85 |

[1]By reverse phase HPLC quantitation.
[2]Combined 1,2-reduction (3,4-dehydrovinblastine, VII) + 1,4-reduction (enamine VIII) products.

TABLE 3

Effect of Temperature on 1,4- vs. 1,2-Reduction of Iminium VI

| Example Numbers | Reduction Procedure | Temperature (° C.) | 1,4:1,2-Reduction Products[1] | Yield[2] (%) |
|---|---|---|---|---|
| 14 | J | +20 | 2.2:1 | 70 |
| 15 | K | −20 | 3.2:1 | 80 |
| 16 | L | −40 | 4.2:1 | 85 |

[1]Quantitation by HPLC.
[2]Combined 1,2-reduction (3,4-dehydrovinblastine, VII) − 1,4-reduction (enamine VIII) products.

Table 2 indicates that the reduction procedures (Procedures I and J as in Examples 13 and 14, respectively) employing reducing agents of Formula IX-I and Formula IX-J afforded the best yields of the enamine (Formula VIII) at 20° C. Table 3 shows the effect of temperature in the reduction of the iminium intermediate (Formula VI) using the reducing agent of Formula IX-J. From Table 3, it is apparent that lowering the reduction temperature to −40° C. (Procedure L, Example 16) from −20° C. (Procedure K, Example 15) resulted in an increase in the ratio of the 1,4-reduction product, versus the 1,2-reduction product, as well as an increase in the overall yield. The results for procedure J (lesser yield and lesser 1,4-reduction product) are consistent with the results for procedures K and L even though procedure J used 5 equivalents of reductant as opposed to 6 equivalents of reductant as used in procedures K and L.

In summary, increased yields of the enamine (Formula VIII) are afforded by employing the 1,4-dihydropyridines of Formula IX wherein $R_1$ is an electron-rich substituent, such as carboxylic esters and carboxylic salts in the 1,4-reduction of the iminium intermediate (Formula VI). The reduction is best conducted under cover with inert conditions such as argon, at a low temperature in the range from about −60° to about +60° C., preferably in the temperature range of from about −60° to +20° C., and most preferably −60° to about −20° C.

The enamine (Formula VIII) formed in the above reduction step (d) may be used directly for subsequent reaction or may be isolated by various chromatographic techniques, for example, the enamine may be isolated by applying the reaction mixture from step (d) directly onto an appropriate chromatographic system such as a column, thin layer or high performance liquid chromatographic system. Preferably reverse phase and/or gel-permeation chromatographic separation methods are employed. The temperature of the isolation procedure may vary from about 4° C. to room temperature. Alternatively, volatile reagents and solvents present in the reaction mixture are removed under reduced pressure and temperature, preferably below −10° C. The resultant residue can be purified by the chromatographic methods described above before further characterization or transformation.

Treatment of the enamine VIII with alkali metal borohydride ($NaBH_4$, $KBH_4$, $LiBH_4$) in accordance with known procedures produces the 4'-deoxoxvinblastine compounds (Formula X, R═$COOCH_3$) and 4'deoxo-4'-epivinblastine compounds (Formula XI, R═$COOCH_3$).

X

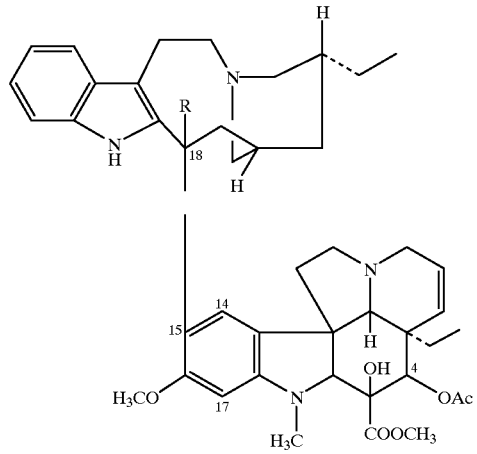

XI

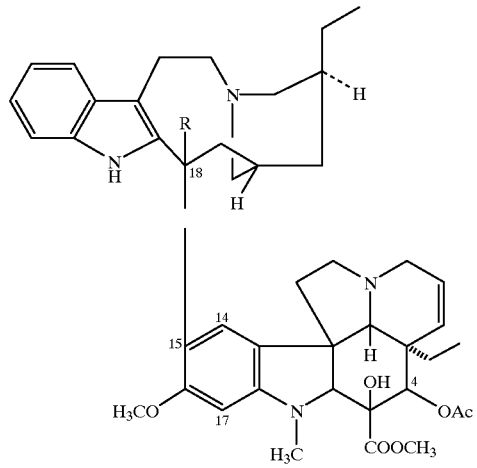

However, under oxidative conditions of the present process step (e) the enamine VIII can be transformed to a second iminium intermediate as represented by Formulae XVI and XVIa.

XVI

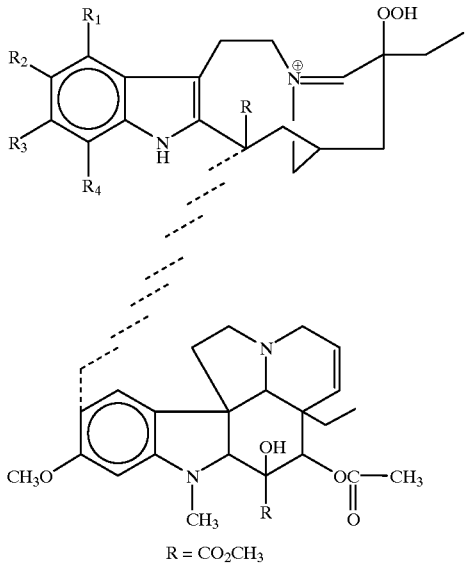

R = $CO_2CH_3$

XVIa

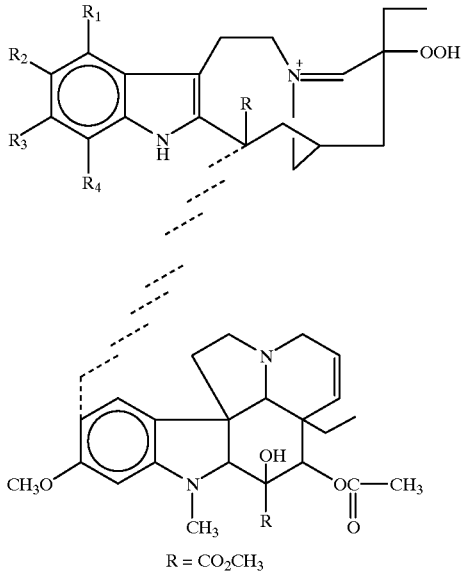

R = $CO_2CH_3$

Oxidative procedures that are useful for converting the enamine (Formula VIII) to the second iminium intermediate (Formulae XVI and XVIa) include, for example:

(1) controlled aeration/oxygenation;

(2) addition of flavin coenzymes (Formula XII):

XII

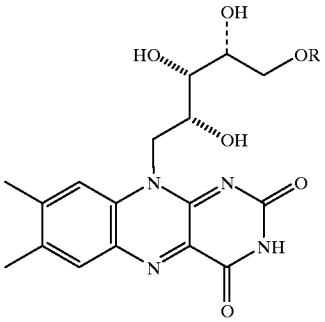

[riboflavin, Formula XII, R=H; flavin mononucleotide (FMN), Formula XII, R=$PO_3^{2-}$; flavin adenine dinucleotide (FAD), Formula XII, R=$(PO_3)_2^2$-adenosine] followed by controlled aeration/oxygenation;

(3) addition of the reduced form of the flavin coenzymes (Formula XIII):

XIII

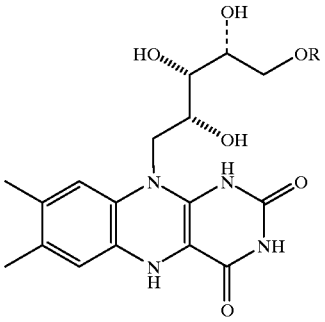

[dihydroriboflavin, Formula XIII, R=H; dihydroflavin, mononucleotide ($FMNH_2$), Formula XIII, R=$PO_3^{2-}$; dihydroflavin adenine dinucleotide ($FADH_2$); Formula XIII, R=$(PO_3)^2$- adenosine], followed by controlled aeration/oxygenation;

(4) addition of a flavin coenzyme, as represented by Formula XII, to generate, in situ, the corresponding 1,5 dihydroflavin coenzyme, as represented by Formula XIII, followed by controlled aeration/oxygenation;

(5) addition of flavin coenzyme analogues having the isoalloxazine structure as represented by Formula XIV:

XIV

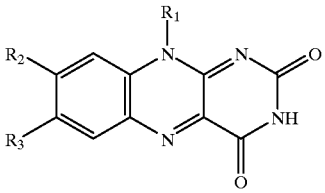

wherein $R_1$, $R_2$ and $R_3$, independently, can be alkyl, substituted alkyl, aryl and substituted aryl functions, followed by controlled aeration/oxygenation;

(6) addition of the reduced form (1,5-dihydro) of the above flavin coenzyme analogues as represented Formula XV:

XV

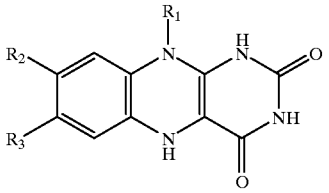

where $R_1$, $R_2$ and $R_3$, independently, can be alkyl, substituted alkyl, aryl and substituted aryl functions, followed by controlled aeration/oxygenation;

(7) addition of hydrogen peroxide and/or hydroperoxides as represented by the Formula R—OOH, where R can be an alkyl, substituted alkyl, aryl or substituted aryl function;

(8) addition of peracids as represented by the Formula R—$CO_3H$, where R can be an alkyl, substituted alkyl, aryl or substituted aryl functions;

(9) addition of superoxides;

(10) addition of a hydroxyl radical (OH) generated in a variety of ways, for example, by the use of hydrogen peroxide in the presence of ferrous ion; or

(11) addition of a metal ion which is a good electron acceptor, for example, ferric ion ($Fe^{+3}$); cupric ion ($Cu^{+1}$), mercuric ion ($Hg_2^{+2}$) and silver ion ($Ag^{+1}$), followed by controlled aeration/oxygenation.

The oxidative procedures (1) and (5)–(10), described above, are conducted in organic solvents such as alcohols, acetonitrile or higher members of this series; dimethyl sulfoxide; dimethylformamide: various ethers such as dioxane, tetrahydrofuran; and aromatic hydrocarbons such as benzene, toluene, etc.

The oxidative procedures involving flavin coenzymes (conditions (2), (3) and (4)), require an aqueous buffer (for example, phosphate, Tris HCl, MES buffers) at pH 5–9, but preferably in the range 6–8, as solvent. An organic co-solvent, e.g. alcohols; acetonitrile or higher members of this series; dioxane; tetrahydrofuran; dimethyl sulfoxide; or dimethylformamide can be used.

The progress of the oxidative procedure is monitored by direct analysis of the reaction mixture on an appropriate chromatographic system, preferably reverse phase high performance liquid chromatography. This method is used to optimize the reaction temperature, time, pressure and concentration of reactants. The reaction temperature may vary from several minutes to several days depending on, for example, the temperature and the particular oxidative conditions. The reaction is generally conducted at atmospheric pressure.

In an alternate embodiment, the enamine solution obtained from the 1,4-reduction of the iminium intermediate (Formula VI) is initially diluted 5–50 fold by the same solvent used in the reduction, at a low temperature (0° C. to −70° C.). The diluted enamine solution is then oxidized (step (e)) to the second iminium intermediates (Formulas XVI and XVIa) by one of the oxidative procedures described hereinabove.

Among the preferred oxidative procedures employed in the present process are:

(a) controlled aeration/oxygenation in which a solution of the enamine is stirred in open air with a stream of air/oxygen bubbled through the solution;

(b) as in step (a), but with addition of ferric chloride;

(c) as in step (a), but with the addition of a flavin coenzyme, as represented by Formula XII, to generate, in situ, the corresponding 1,5-dihydroflavin coenzyme, as represented by Formula XIII; or (d) as in step (a), but with the addition of hydrogen peroxide and/or hydroperoxides as represented by the Formula R—OOH where R is alkyl or aryl.

The oxidative procedures are conducted in organic solvents such as alcohols; acetonitrile or higher members of this series; dimethyl sulfoxide; dimethyformamide; ethers such as dioxane; tetrahydrofuran; aromatic hydrocarbons such as benzene, toluene, etc. An aqueous buffer (e.g., phosphate, Tris-HCl, MES buffers) at pH 5–9, but preferably in the range of 6–8, can be used as co-solvent. The reaction temperatures may vary from about −60° to about +60° C.

Various parameters for the oxidative transformation step (e) have been studies to optimize the yield of the target compounds, particularly vinblastine (Formula I). The results of these studies have been illustrated in Tables 4–7, as follows:

TABLE 4

Effect of Ferric Chloride on Production of Vineblastine from Enamine VIII[3]

| Amount of $FeCl_3$ (Equivalents) | Oxidation Conditions (Temp., time) | % Yield of Vinblastine[2] |
|---|---|---|
| 0 | Air[1], 0° C., 5 min | 0 |
| 1 | Air[1], 0° C., 5 min | 13.3 |
| 2 | Air[1], 0° C., 5 min | 19.0 |
| 3 | Air[1], 0° C., 5 min | 10.4 |

[1]At a rate of 60 ml/min.

[2]By reverse-phase HPLC quantitation, after reductive work-up with $NaBH_4$.

[3]Enamine VIII generated at −40° C. (Procedure L).

TABLE 5

Effect of Time of Oxidation on Production of Vineblastine from Enamine VIII[3]

| Time[1] (min) | % Yield of Vinblastine[2] |
|---|---|
| 1 | 8.2 |
| 5 | 15.4 |
| 10 | 15.5 |
| 15 | 15.7 |
| 45 | 6.5 |

[1]Reaction conditions: −2 eq. ferric chloride added, air bubbled through the solution at 60 ml/min at 0° C.

[2]By reverse-phase HPLC quantitation after reductive work-up with $NaBH_4$.

[3]Enamine VIII generated at −40° C. (Procedure L).

TABLE 6

Effect of Oxidation Temperature on Production of Vineblastine from Enamine VIII[3]

| Temp., ° C.[1] | % Yield of Vinblastine[2] |
|---|---|
| −40 | 3.7 |
| −23 | 6.2 |
| 0 | 19.6 |
| 20 | 20.6 |
| 45 | 16.0 |

[1]Reaction conditions: 2 eq. ferric chloride added, air bubbled through the solution at 60 ml/min for 15 min.
[2]By reverse-phase HPLC quantitation after reductive work-up with $NaBH_4$.
[3]Enamine VIII generated at −40° C. (Procedure L).

TABLE 7

Effect of Dilution on Production of Vineblastine from Enamine VIII[3]

| Dilution Factor[1,4] | % Yield of Vinblastine[2] |
|---|---|
| 1 | 19.6 |
| 5 | 25.2 |
| 10 | 30.1 |
| 20 | 29.6 |
| 50 | 24.7 |

[1]Reaction conditions: 2 eq. ferric chloride added, air bubbled through the solution at 60 ml/min for 15 min at 0° C.
[2]By reverse-phase HPLC quantitation after reductive work-up with $NaBH_4$.
[3]Enamine generated at −40° C. (Procedure L).
[4]Dilution Factor 1 = 100 mg Iminium VI in 6 ml methanol to which reducing agent Formula IX-J (6 eq.) in 6 ml methanol was added. (Total volume = 12 ml) Dilution Factor 5 = Total volume of 60 ml; Dilution Factor 10 =0 Total volume of 120 ml; Dilution Factor 20 = Total volume 240 ml; Dilution Factor 50 = Total volume of 600 ml.

Table 4, which indicates the effect of ferric chloride concentration on the yield of vinblastine (I), shows that the yield first increases and then decreases with increasing ferric chloride concentration. Maximum vinblastine yield is seen to occur at a ferric chloride concentration of about two equivalents.

Table 5, which sets forth the results relating to the yield of vinblastine (I) versus the time of oxidation, indicates that the maximum yield of vinblastine (I) is reached after about 5 to about 15 minutes of aeration in the presence of 2 equivalents of ferric chloride and that the yield significantly decreases with an oxidation time of 45 minutes.

Table 6, which sets forth the results of various oxidation temperatures on the yield of vinblastine (I), shows that a temperature in the range of from about 0° to about 20° C. provides the highest yield of vinblastine (I) after a reductive work-up with $NaBH_4$, as quantified by reverse-phase HPLC.

Table 7, which sets forth the effect of dilution of the enamine (VIII) solution on the production of vinblastine (I), shows that a dilution factor of about 5 to about 20 on the enamine (VIII) solution before aeration in the presence of ferric chloride (2 equivalents) at 0° C., affords the best yield of vinblastine (I) as quantified by reverse-phase HPLC after reductive work-up with $NaBH_4$.

Summarizing the results set forth in Tables 4–7, in the oxidative transformation (step (e)) of the enamine, the dilution factor of the enamine solution obtained in the 1,4-reduction (step (d)) of iminium intermediate (Formula VI), by the same solvent used in the reduction, is preferably in the range of 5 to 20 fold and most preferably about 10 fold (8 to 12 fold). The dilution procedure is conducted at a low temperature (from about 0° to about −70° C.), preferably below about −40° C. and under inert cover such as argon. The oxidative transformation of the enamine is best carried out within the following parameters: (1) aeration at about 60 ml/min for 5 to 20 minutes, and preferably about 15 minutes; (2) at a temperature in the range from about 0° to about 20° C. and preferably about 20° C. (3) in the presence of about 2 equivalents of ferric chloride, to afford the corresponding second iminium intermediates (Formulae XVI and XVIa).

Reduction of these second iminium intermediate (Formulae XVI and XVIa) in step (f) by reaction with an alkali metal borohydride ($NaBH_4$, $KBH_4$, $LiBH_7$, etc.) lead to the target compounds vinblastine and leurosidine, and the by-products 3',4'-dehydrovinblastine (Formula VII), leurosine (Formula XVII), catharine (Formula XVIII), vinamidine (Formula XIX) and the reduction product of vinamidine (Formula XX).

XVII

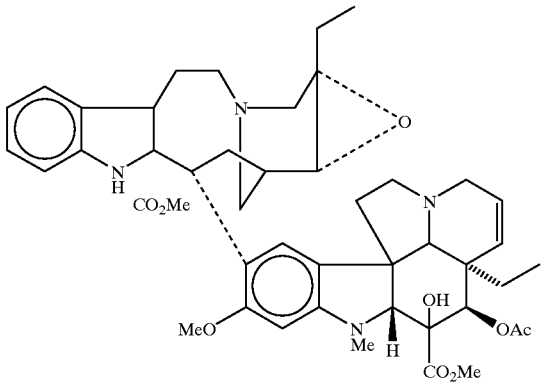

XVIII

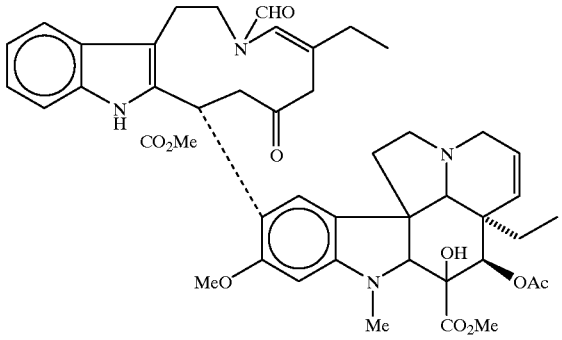

XIX

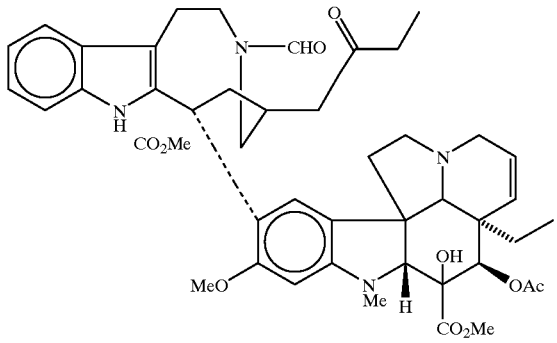

-continued

XX

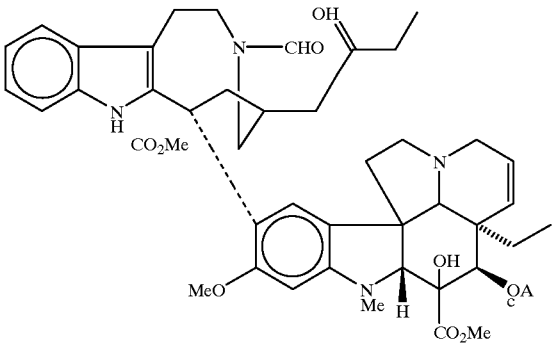

The reduction is carried out in suitable solvents (organic and inorganic), such as those described above in the oxidative transformation step (e). The reduction is conducted at low temperature, in the range from about −20° C. to about 4° C., and preferably at about 0° C. and at a pH lower than 8.5, and preferably between about 7.5 and 8. The total reaction mixture may then be concentrated in vacuo at a low temperature in the range from about 0° to about 10° C. before extraction and isolation of the target compound.

The following examples (Examples 17–21, methods 1–5) described the synthesis of vinblastine by oxidation of the enamine (Formula VIII).

EXAMPLE 17

Synthesis of Vinblastine (Formula I) by Oxidation of Enamine (Formula VIII) to Iminium Intermediate (Formula XVI) with Flavin Mononucleotide (FMN Formula XII R=$PO_3^{-2}$)—Method 1

To a stirred reaction mixture containing 100 mg of the enamine (VIII) obtained as described above (Example 2, Procedure A) from the iminium intermediate VI there was added FMN (80 mg, 1 equivalent) dissolved in Tris HCL buffer (2 ml) under a positive atmosphere (greater than 760 mm Hg) of argon. The solution was kept in the dark at room temperature (20° C.) for 16 hours. After this time, the inert atmosphere of argon was replaced by air the reaction mixture was stirred for another 2.5 hours. Reverse phase HPLC analyses indicated transformation of the enamine VIII to the iminium intermediate XVI as well was to other by-products. Sodium borohydride (500 mg) was added at 0° C. and the reaction mixture was made basic with $NH_4OH$ and extracted with ethyl acetate (3×200 ml). The combined organic extract was dried over magnesium sulphate and the solvent was removed in vacuo to provide a crude product (85 mg). Purification of the crude product by thick layer chromatography (silica gel, methanol; ethyl acetate 1:5) allowed the separation of the following dimeric products: vinblastine (Formula I, 22 mg, 23%); 3',4'-dehydrovinblastine (Formula VII, 16 mg, 17%); leurosine (Formula XVII, 8 mg, 9%), catharine (Formula XVIII, 7 mg, 7.5%) vinamidine (Formula XIX, 5 mg, 5.6%) and the reduction product of vinamideint (Formula XX, 19 mg, 20%)

EXAMPLE 18

Synthesis of Vinblastine (Formula I) by Oxidation of the Enamine (Formula VIII) with Hydrogen Peroxide to the Iminium Intermediate (Formula XVI)—Method 2

To a solution containing 100 mg of the enamine (VIII) obtained from iminium intermediate VI (Example 2, Procedure A) there was added hydrogen peroxide (30%, 1.2 ml, 95 equivalents) under an inert atmosphere of argon. The reaction mixture was stirred at room temperature for 5.5 hours when reverse phase HPLC analyses indicated complete conversion of enamine VIII. Sodium borohydride (500 mg) was added at 0° C. and the resulting solution was extracted with ethyl acetate (3×200 ml). The combined organic extract was dried over magnesium sulfate and removed in vacuo. The resulting product mixture was separated by thick layer chromatography (silica gel, methanol/ethyl acetate) to give the following dimeric alkaloids: vinblastine (I, 4 mg, 4%), 3',4'-dehydrovinblastine (VII, 5 mg, 4.8%), leurosine (XVII, 13 mg, 12.5%), catharine (XVIII, 5 mg, 4.8%), the reduced form of vinamidine (XX, 30 mg, 27.6%)

EXAMPLE 19

Synthesis of Vinblastine (I) by Oxidation of the Enamine (VIII) with Air to the Iminium Intermediate (Formula XVI)—Method 3

A solution containing 100 mg of the enamine (VIII) obtained from the iminium intermediate VI, (Example 2, Procedure A) was stirred in open air at room temperature for 3 hours. After this time, sodium borohydride (500 mg) was added at 0° C. and the reaction mixture was made basic with $NH_4OH$ and extracted with ethyl acetate (3×200 ml). The combined organic extract was dried over $MgSO_4$ and removed in vacuo. The resulting crude product was separated by thick layer chromatography (silica gel, methanol/ethyl acetate) to give vinblastine (I, 4 mg, 4%).

EXAMPLE 20

Synthesis of Vinblastine (I) by Oxidation of the Enamine (Formula VIII) with Air in the Presence of Ferric Chloride, to the Iminium Intermediate (XVI)—Method 4

To a stirred solution containing 100 mg the enamine (VIII) obtained from the iminium intermediate VI (Example 2, Procedure A) there was added ferric chloride (1 equivalent) and air bubbled through the solution at 0° C. for a period of 0.5 hours. Sodium borohydride (500 mg) was added at 0° C. and the reaction mixture was made basic with $NH_4OH$ before extraction with ethyl acetate (3×100 ml). The combined organic extract was dried over $Na_2SO_4$ and the solvent was removed in vacuo. The crude product was purified by thick layer chromatography (silica gel, methanol/ethyl acetate) to give vinblastine (I, 37 mg). Based on enamine (50 mg) present in the mixture, the yield of vinblastine was 70%.

EXAMPLE 21

Synthesis of Vinblastine (Formula I) by oxidation of Enamine (Formula VIII) to Iminium Intermediate (Formula XVI) with air in the presence of Ferric Chloride at high dilution. (Method 5).

A solution containing 200 mg of enamine (VIII) obtained from the iminium intermediate VI (Example 16, Procedure L) was diluted five-fold with methanol before oxidation (total vol.: 120 ml). Ferric chloride (75 mg, 2 equivalents) was then added, and the solution was concentrated in vacuo before adding water (100 ml) and extracting with ethyl acetate (3×200 ml). The combined organic extract was dried over $Na_2SO_4$ and the solvent was evaporated in vacuo. The crude product was purified by column chromatography (silica gel, TLC grade, 15 g). Elution with ether: chloroform (10:7) gave 3',4'-dehydrovinblastine (VII, 18 mg, 11%). Further elution with ether:chloroform:methanol (10:7:0.5) gave vinblastine (I, 62 mg, 37%).

For practical purposes, isolation of the intermediates (V, VI, VIII, XVI, XVIa) is not required and the entire process for the indole unit Formula III) and the dihydroindole unit (Formula IV) is preferably conducted in a one-pot operation as illustrated in Example 22.

EXAMPLE 22

One-Pot Conversion of Catharanthine (Formula III, $R_1$, $R_2$, $R_3$, and $R_4$=H, R=$COOCH_3$) and Vindoline (Formula III) to Vinblastine (Formula I) and Leurosidine-Overall Procedure To a solution of catharanthine (500 mg, 1.5 mmol) in dry dichloromethane (4.5 ml) at −15 C. under a positive atmosphere (greater than 760 mm Hg) of argon there was added m-chloroperbenzoic acid (330 mg, 1.9 mmol) in one portion, and the mixture was stirred at 10° to −15° C. for 5 minutes. After this time, the reaction mixture was cooled to −40° C. and a solution of vindoline (IV, 450 mg, 1 mmol) in dry dichloromethane (1 ml) was added, followed immediately by trifluoroacetic anhydride (1 ml, 7.1 mmol). After 2 hours at −60° C. volatiles were removed in vacuo (high vacuum pump) and dry, degassed methanol (12 mol) was added after flushing the system with argon. The resulting orange solution was cooled to −40° C. and a solution of 1,4-dihydro-1-(sodium-isobutyl-1-carboxylate)-nicotinamide (Formula IX-J) (1.5 g. 6 mmol) in dry degassed methanol (12 ml) was added under a positive atmosphere of argon. After reduction was complete (by reverse-phase HPLC monitoring), cold methanol (about 300 ml) was added, keeping the temperature of the solution between about −5° to about 0° C. Ferric chloride (330 mg, 2 mmol) was then added and dry air was bubbled through the solution at a rate of about 60 ml/min for a period of 20 min. Sodium borohydride (1 g) was added and the solution concentrated in vacuo (water aspirator) before adding water (100 ml) and extracting with ethyl acetate (3×150 ml). The combined organic extract was dried over $Na_2SO_4$ and the solvent was evaporated in vacuo to give the crude product which was purified by chromatography as previously described to give 3',4'-dehydrovinblastine (VII, 95 mg, 12%), vinblastine (315 mg, 39%) and leurosidine (130 mg, 16%).

In summary, the present invention significantly differs from the prior art in several important steps, specifically the characterization of the unstable intermediates V, VI, VIII, XVI and XVIa. These intermediates can be isolated, but isolation is not essential and the entire process, monitored carefully for said intermediates, can be conducted in a one pot operation, as illustrated in reaction scheme IV.

REACTION SCHEME IV

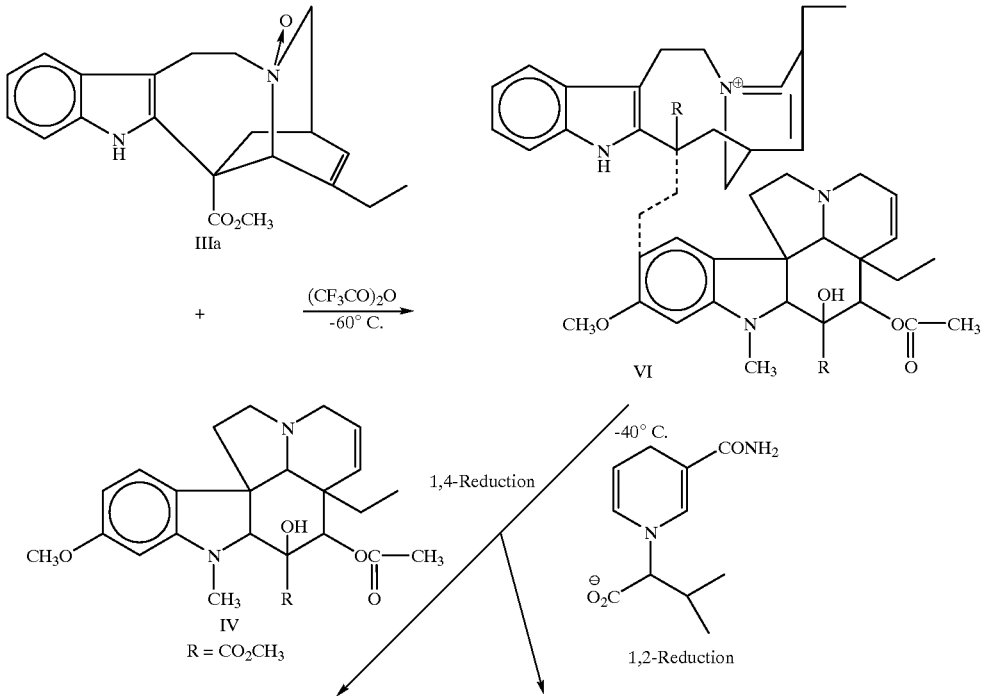

-continued
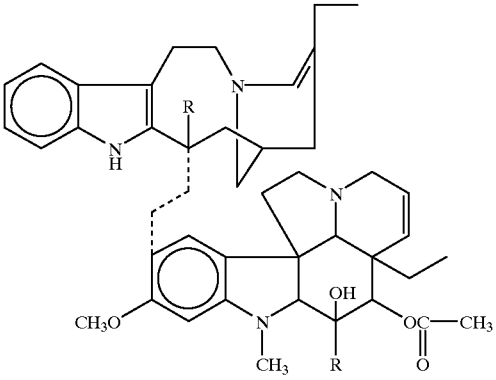
VIII
Enamine
+
Ratio 4.2:1
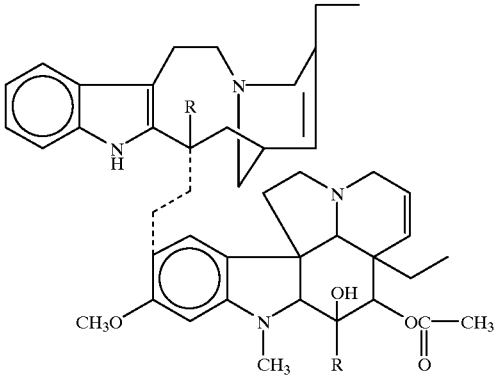
Anhydrovinblastine
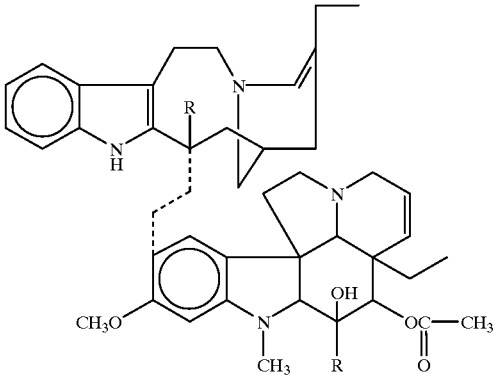
VIII
R = $CO_2CH_3$
$FeCl_3$ (2 equiv.), 0° C.
Air, 60 ml/min, 15 min
Dilution Factor 10

-continued

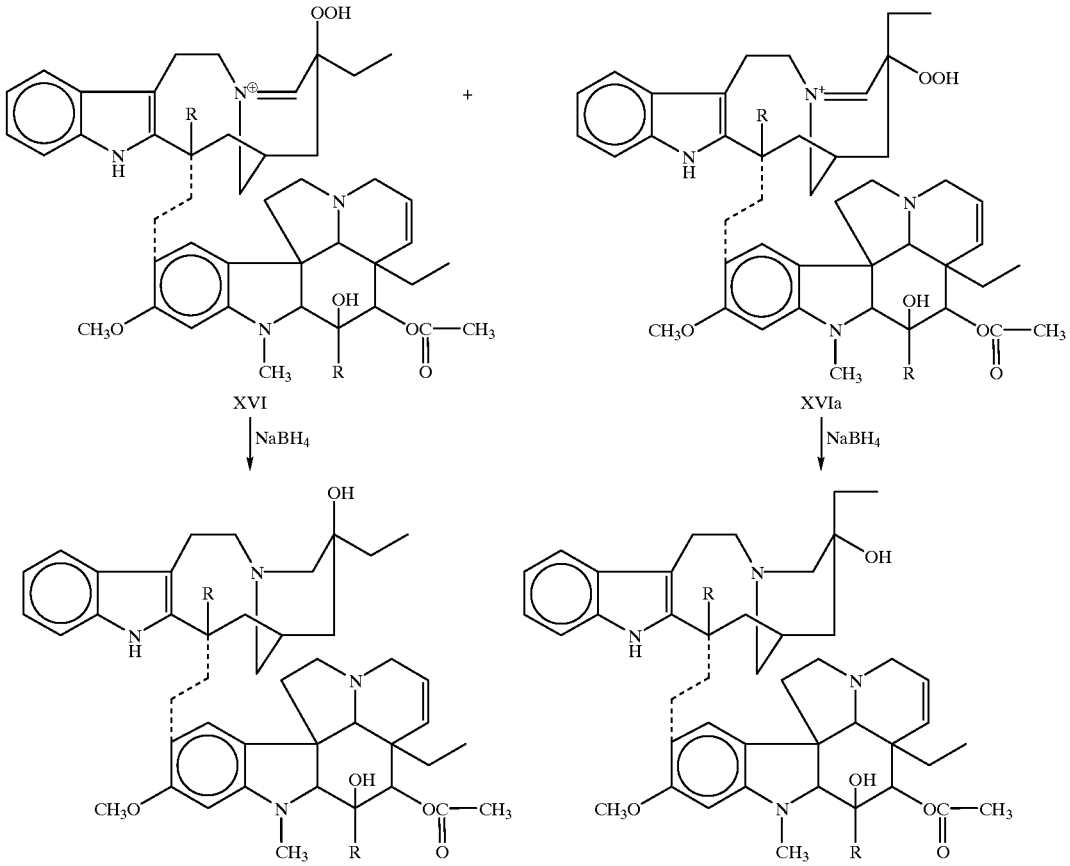

Overall Yield: Vinblastine (42 %); Leurosidine (17 %); Anhydrovinblastine (18 %)

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for the production of dimer alkaloid compounds comprising the steps of:

(a) oxidizing an indole unit having a bridge nitrogen and being represented by the following formula:

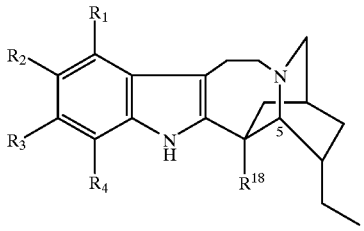

wherein R represents hydrogen or COO-alkyl and $R_1$, $R_2$, $R_3$ and $R_4$ independently represent H, OH, O-alkyl, OCO-alkyl, alkyl or aryl groups, said oxidation being carried out in the cold, at a temperature from about −77° C. to about +40° C, thereby oxidizing the bridge nitrogen of said indole unit and forming an N-oxide derivative as represented by the following formula:

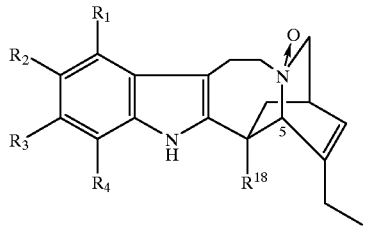

wherein $R_1$, $R_2$, $R_3$, and $R_4$ are the same as above, and without isolating said derivative;

(b) treating said N-oxide derivative in the presence at least of one member selected from of the group consisting of acetic anhydride, halogenated acetic anhydride, and acetyl chloride, to effect a Polonovski-type fragmentation reaction;

(c) without isolating the product of step (b), stereoscopically coupling said product of step (b) with a dihydroindole unit represented by the formula:

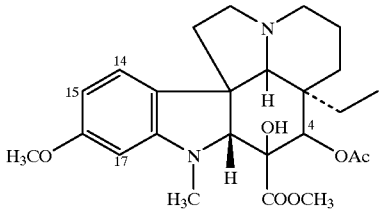

said coupling being conducted in the presence of at least one member selected from the group consisting of acetic anhydride, halogenated acetic anhydride, and acetyl chloride at a low temperature of about −70° to about +40° C., under inert conditions, to form a first iminium intermediate, represented by the formula:

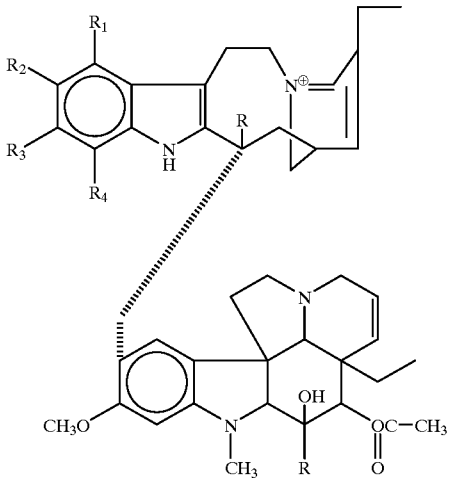

wherein R═$COOCH_3$ and $R_1$, $R_2$, $R_3$, and $R_4$ are the same as defined above;

(d) reducing said first iminium intermediate by reaction with a 1,4-dihydropyridine compound, thereby forming an enamine intermediate, represented by the following formula:

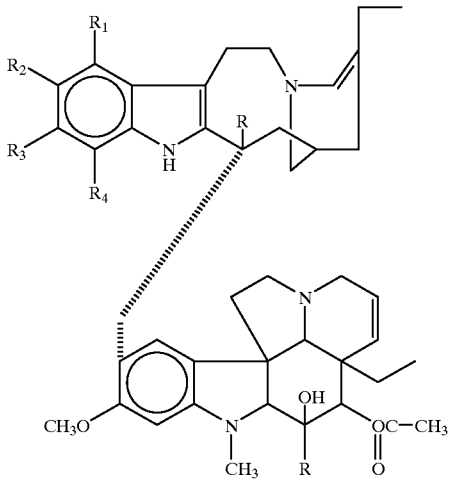

wherein R═COOCH, and $R_1$, $R_2$, $R_3$, and $R_4$ are the same as defined in step (c);

(e) transforming said enamine intermediate obtained in step (d) by oxidation under controlled aeration conditions to a second iminium intermediate, as represented by the following formula:

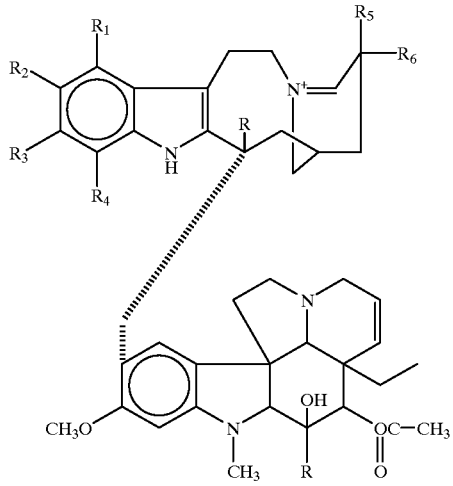

wherein R═$COOCH_3$ and $R_1$, $R_2$, $R_3$, and $R_4$ are the same as defined in step (c), $R_5$ is OOH or $C_2H_5$ and $R_6$ is OOH or $C_2H_5$, with the proviso that $R_5$ and $R_6$ cannot be the same; and (f) reducing the second iminium intermediate obtained in step (e) to form said dimer alkaloid compounds, represented by the formula:

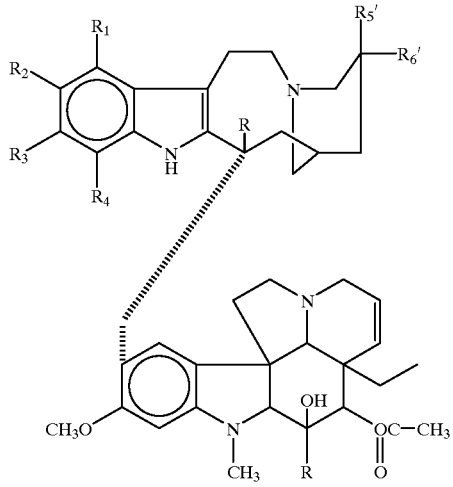

wherein R, $R_1$, $R_2$, $R_3$, $R_4$, $R_5$ and $R_6$ are the same as defined in step(e) and $R'_5$ and $R'_6$ are OH or $C_2H_5$, with the proviso that $R'_5$ and $R'_6$ cannot be the same.

2. The process according to claim 1, further including the step of diluting said enamine obtained in step (d) by a factor of 5 to 50 with a solvent fold prior to performing step (e).

3. The process according to claim 1, wherein the 1,4-dihydropyridine compound that is used in step (d) to reduce said first iminium intermediate is represented by the following formula:

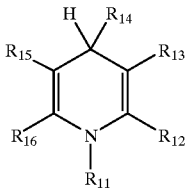

wherein $R_{11}$ is H, alkyl, arylalkyl, diarylalkyl, alkoxy, alkoxy, alkoxycarbonylalkyl, dialkoxycarbonylalkyl, alkali metal salts thereof, aryl, and sugar units;

$R_{12}$, $R_{14}$ and $R_{16}$, independently, are H, alkyl or aryl;

$R_{13}$ is H, alkyl, carboxylate and salts thereof, aryl, cyano, $CONR_{17}R_{18}$ wherein $R_{17}$ and $R_{18}$ independently may be H, alkyl, aryl, or taken together, $R_{17}$ and $R_{18}$ can form a ring structure containing up to four carbon atoms, said ring structure may further be substituted by $CONR_{19}R_{20}$, wherein $R_{19}$ and $R_{20}$ are H or alkyl; and $R_{15}$ may be H, alkyl, carboxylate and salts thereof, and aryl.

4. The process according to claim 3, wherein $R_{13}$ and $R_{15}$ are carboxylate.

5. The process according to claim 3, wherein $R_{13}$ is $CONR_{17}R_{18}$ wherein $R_{17}$ and $R_{18}$ independently may be H, alkyl, aryl, or taken together, $R_{17}$ and $R_{18}$ can form a ring structure containing up to four carbon atoms, said ring structure may further be substituted by $CONR_{15}R_{20}$, wherein $R_{19}$ and $R_{20}$ are H or alkyl.

6. The process according to claim 5, wherein $R_{11}$ is an electron-donating substituent selected from the group consisting of alkyl, aryl, carboxy, carboxylate and salts thereof, and sugar units.

7. The process according to claim 6, wherein $R_1$ is selected from the group consisting of carboxylic esters and carboxylate salts.

8. The process according to claim 7, wherein $R_1$ is 1',2'-di (methoxy carbonyl) ethyl.

9. The process according to claim 7, wherein $R_1$ is sodium-isobutyl-1-carboxylate.

10. The process of claim 1, wherein the reduction of step (d) is conducted in an inert atmosphere at a temperature in the range from about −60° to about +60° C. in the presence of at least one solvent selected from the group consisting of lower alkyl alkanols, acetonitrile, dimethyl sulfoxide, dimethylformamide, dioxane, tetrahydrofuran, and chlorinated lower hydrocarbons.

11. The process according to claim 10, wherein the reduction of step (d) is conducted at a temperature in the range of about −20° to about −60° C.

12. The process according to claim 1 wherein the oxidative transformation step (e) is selected from the group consisting of:

(1) controlled aeration/oxygenation in which a solution of said enamine is stirred in open air or with a stream of air/oxygen bubbled through the solution;

(2) controlled aeration/oxygenation in which a solution of said enamine and a metal ion, selected from the group consisting of ferric ion ($Fe^{+3}$), cupric ion ($Cu^{+2}$), cuprous ion ($Cu^{+1}$), mercuric ion ($Hg_2^{+2}$) and silver ion ($Ag^{+1}$) is stirred in open air or with a stream of air/oxygen bubbled through the solution;

(3) controlled aeration/oxygenation in which a solution of said enamine and a flavin coenzyme is stirred in open air or with a stream of air/oxygen bubbled through the solution;

(4) controlled aeration/oxygenation in which a solution of said enamine and a flavin coenzyme is stirred in open air or with a stream of air/oxygen bubbled through the solution, wherein the flavin coenzyme generates, in situ, the corresponding 1,5-dihydroflavin coenzyme;

(5) controlled aeration/oxygenation in which a solution of said enamine and a member selected from the group consisting of hydrogen peroxide and hydroperoxides represented by the Formula R—OOH, where R is alkyl or aryl and mixtures thereof is stirred in open air or with a stream of air/oxygen bubbled through the solution (G) said aeration/oxidation being conducted in an organic solvent at a pH of 5–9 and a reaction temperature of about −60° to about +60° C.

13. The process according to claim 12, wherein the oxidative transformation step (e) is conducted at a pH in the range of 6–8.

14. The process according to claim 12, wherein about two equivalents of ferric chloride are employed in step (e) (2).

15. The process according to claim 12, wherein the time of aeration in the oxidative transformation step (e) is from bout five to about twenty minutes.

16. The process according to claim 12, wherein the oxidative transformation step (e) is conducted at a temperature in the range from about 0° to about 20° C.

17. The process according to claim 2, wherein said enamine obtained in step (d) is diluted from about 5 to about 20 fold with a solvent, prior to performing step (e).

18. The process according to claim 17, wherein said enamine is diluted 8 to 12 fold.

19. The process according to claim 1, wherein said reduction step (f) is conducted at a temperature in the range from about 4° to about −20° C., and at a pH between about 7.5 and about 8.5, and wherein the reaction mixture in step (f) is concentrated in vacuo at a temperature between about 0° and about 10° C. before extraction and isolation of the target compound.

20. The process according to claim 1, wherein the reducing used in step (f) comprises contacting the reaction product from step (e) with an alkali metal borohydride selected from the group consisting of $NaBH_4$, $KBH_4$ and $LiBH_4$.

21. The process according to claim 1, wherein steps (a)–(f) are conducted in a one-pot operation without isolation of any intermediate products.

22. The process according to claim 1, wherein at least one of the intermediates formed in steps (c), (d) and (e) is isolated prior to being further reacted.

23. The process according to claim 22, wherein each of said intermediates formed in steps (c), (d) and (e) isolated prior to being further reacted.

24. A process according to claim 1, wherein the dimer alkaloid compound is vinblastine.

25. A process according to claim 24, further comprising the step of oxidizing said vinblastine to obtain the dimer alkaloid compound vincristine.

26. A process according to claim 1, wherein the dimer alkaloid compound is leurosidine.

27. A process for the production of dimer alkaloid compounds comprising the steps of:

(a) forming an N-oxide derivative in the cold, at a temperature from about −77° to about +40° C. from an indole unit having a bridge nitrogen by oxidizing the bridge nitrogen and without isolating said derivative;

(b) treating said N-oxide derivative in the presence at least of one member selected from the group consisting of acetic anhydride, halogenated acetic anhydride, and acetyl chloride, to effect a Polonovski-type fragmentation reaction;

(c) without isolating the product of step (b), stereospecifically coupling said product of step (b) with a dihydroindole unit in the presence of at least one member selected from the group consisting of acetic anhydride, halogenated acetic anhydride, and acetyl chloride at a low temperature of about −70° to about +40° C., under inert conditions, to form a first iminium intermediate;

(d) reducing said first iminium intermediate by reaction with a 1,4-dihydropyridine compound, thereby forming an enamine intermediate;

(e) preparing a second iminium intermediate by oxidative transformation of said enamine intermediate obtained in step (d) under controlled aeration conditions; and (f) reducing the product obtained in step (e) to form dimer alkaloid compounds represented by the formula:

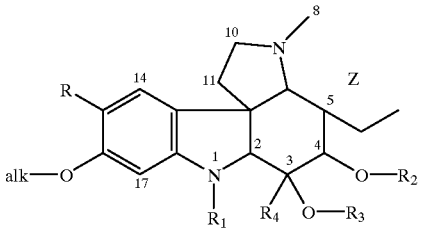

wherein:

alk=$CH_3$ or $(CH_2)_n$ $CH_3$ where n=1–5;

$R_1$=$CH_3$ $R_2$=H or CO-alk;

$R_3$=H;

$R_4$=COO-alk or $CONR_{13}R_{14}$ wherein $R_{13}$ and $R_{14}$ are selected from the group consisting of hydrogen, alkyl, substituted alkyl, aryl or substituted aryl;

Z=—CH═CH— or —$CH_2$—$CH_2$—;

R=II or IIa;

II

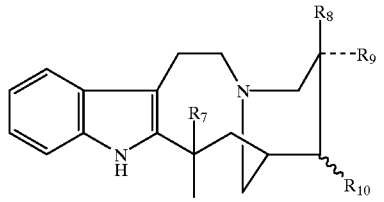

IIa

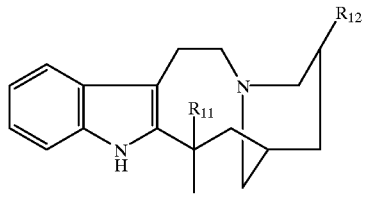

and wherein, $R_7$=H or COO-alk;

$R_8$=H, OH, O-alk, OCO-alk or alkyl;

$R_9$=H, OH, O-alk, OCO-alk or alkyl;

$R_{10}$=H, OH, O-alk, OCO-alk;

$R_{11}$=H or COO-alk; and $R_{12}$=H or alkyl.

28. The process according to claim 27, further including the step of diluting said enamine obtained in step (d) by a factor of 5 to 50 with a solvent fold prior to performing step (e).

29. The process according to claim 27, wherein the 1,4-dihydropyridine compound that is used in step (d) to reduce said first iminium intermediate is represented by the following formula:

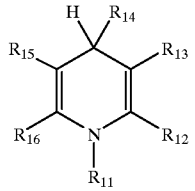

wherein $R_{11}$ is H, alkyl, arylalkyl, diarylalkyl, alkoxy, alkoxy, alkoxycarbonylalkyl, dialkoxycarbonylalkyl, alkali metal salts thereof, aryl, and sugar units;

$R_{12}$, $R_{14}$ and $R_{16}$, independently, are H, alkyl or aryl;

$R_{13}$ is H, alkyl, carboxylate and salts thereof, aryl, cyano, $CONR_{17}R_{18}$ wherein $R_{17}$ and $R_{18}$ independently may be H, alkyl, aryl, or taken together, $R_{17}$ and $R_{18}$ can form a ring structure containing up to four carbon atoms, said ring structure may further be substituted by $CONR_{19}R_{20}$, wherein $R_{19}$ *1 and* $R_{20}$ are H or alkyl;

$R_{15}$ may be H, alkyl, carboxylate and salts thereof, and aryl.

30. The process according to claim 27, wherein $R_{13}$ and $R_{15}$ are carboxylate.

31. The process according to claim 29, wherein $R_{13}$ is $CONR_{17}R_{18}$ wherein $R_{17}$ and $R_{18}$ independently may be H, alkyl, aryl, or taken together, $R_{17}$ and $R_{18}$ can form a ring structure containing up to four carbon atoms, said ring structure may further be substituted by $CONR_{19}$ $R_{20}$, wherein $R_{19}$ and $R_{20}$ are H or alkyl.

32. The process according to claim 31, wherein $R_{11}$ is an electron-donating substituent selected from the group consisting of alkyl-aryl, carboxy, carboxylate and salts thereof, and sugar units.

33. The process according to claim 32, wherein $R_1$ is selected from the group consisting of carboxylates and carboxylate salts.

34. The process according to claim 6 wherein the oxidative transformation step (e) is selected from the group consisting of:

(1) controlled aeration/oxygenation in which a solution of said enamine is stirred in open air or with a stream of air/oxygen bubbled through the solution;

(2) controlled aeration/oxygenation in which a solution of said enamine and a metal ion, selected from the group consisting of ferric ion ($Fe^{+3}$), cupric ion ($Cu^{+2}$), cuprous ion ($Cu^{+1}$), mercuric ion ($Hg_2^{+2}$) and silver ion ($Ag^{+1}$) is stirred in open air or with a stream of air/oxygen bubbled through the solution;

(3) controlled aeration/oxygenation in which a solution of said enamine and a flavin coenzyme is stirred in open air or with a stream of air/oxygen bubbled through the solution;

(4) controlled aeration/oxygenation in which a solution of said enamine and a flavin coenzyme is stirred in open air or with a stream of air/oxygen bubbled through the solution, wherein the flavin coenzyme generates, in situ, the corresponding 1,5-dihydroflavin coenzyme;

(5) controlled aeration/oxygenation in which a solution of said enamine and a member selected from the group consisting of hydrogen peroxide and hydroperoxides represented by the Formula R—OOH, where R is alkyl or aryl and mixtures thereof is stirred in open air or with a stream of air/oxygen bubbled through the solution (G) said aeration/oxidation being conducted in an organic solvent at a pH of 5–9 and a reaction temperature of about −60° to about +60° C.

35. The process according to claim 27, wherein the reducing used in step (f) comprises contacting the reaction product from step (e) with an alkali metal borohydride selected from the group consisting of $NaBH_4$, $KBH_4$ and $LiBH_4$.

36. The process according to claim 27, wherein steps (a)–(f) are conducted in a one-pot operation without isolation of any intermediate products.

37. A process according to claim 27, wherein the dimer alkaloid compound is vinblastine.

38. A process according to claim 37, further comprising the step of oxidizing said vinblastine to obtain the dimer alkaloid compound vincristine.

39. A process according to claim 27, wherein the dimer alkaloid compound is leurosidine.

*40. The process according to claim 1, wherein 3',4'-anhydrovinblastine is isolated following any one of steps (d), (e) or (f).*

* * * * *